United States Patent
Atkinson et al.

(10) Patent No.: US 6,784,337 B1
(45) Date of Patent: Aug. 31, 2004

(54) METHOD OF IMPROVING NEMATODE RESISTANCE IN PLANTS VIA TRANSFORMATION WITH A DNA ENCODING A PROTEINASE INHIBITOR FUSION PROTEIN

(75) Inventors: Howard John Atkinson, Nr Settle (GB); Michael John McPherson, Thornhill (GB); Peter Edward Urwin, Bramley (GB)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 09/554,941

(22) PCT Filed: Dec. 1, 1998

(86) PCT No.: PCT/EP98/07792

§ 371 (c)(1),
(2), (4) Date: Mar. 22, 2000

(87) PCT Pub. No.: WO99/28484

PCT Pub. Date: Jun. 10, 1999

(30) Foreign Application Priority Data

Dec. 3, 1997 (GB) ............................................. 9725556

(51) Int. Cl.$^7$ .............................................. C12N 15/82
(52) U.S. Cl. ...................................................... 800/279
(58) Field of Search ................................. 800/229, 257, 800/301, 302, 279; 435/418, 419, 320.1; 536/23.2

(56) References Cited

U.S. PATENT DOCUMENTS

| | | | |
|---|---|---|---|
| 5,380,831 A | 1/1995 | Adang et al. ............. | 536/23.71 |
| 5,436,392 A | 7/1995 | Thomas et al. ............. | 800/205 |
| 5,461,032 A | 10/1995 | Krapcho et al. ............... | 514/12 |
| 5,837,876 A | * 11/1998 | Conkling et al. ........... | 800/205 |
| 6,031,087 A | * 2/2000 | Anderson et al. .......... | 536/23.2 |

FOREIGN PATENT DOCUMENTS

| | | | |
|---|---|---|---|
| EP | 92301890.7 | * | 5/1992 |
| EP | 0 497 366 | | 8/1992 |
| WO | 92 15690 | | 9/1992 |
| WO | 94 13810 | | 6/1994 |
| WO | 96 10083 | | 4/1996 |
| WO | 96 16173 | | 5/1996 |
| WO | 97 20057 | | 6/1997 |

OTHER PUBLICATIONS

Gleddie et al., The Control of Plant Phathogens with Protease Inhibitors, Chapter 5, pp. 53–63.*

Lilley, C.J., et al., Parasitology, 113 (Pt4):415–425 (Oct. 1996).

Urwin et al., Plant Journal, 12(2):455–461 (1997).

Urwin et al., Planta, 204:472–479 (Apr. 1998).

* cited by examiner

*Primary Examiner*—Anne R. Kubelik
(74) *Attorney, Agent, or Firm*—Mary Kakefuda

(57) ABSTRACT

The invention is directed to a method for improving resistance or tolerance of a plant to a pathogen, wherein the method comprises integrating a DNA molecule encoding a fusion protein comprising at least two anti-pathogenic proteins or protein domains joined by at least one linker peptide, wherein the first anti-pathogenic protein or protein domain comprises Oc-IΔD86 or Oc-I and the second anti-pathogenic protein or protein domain comprises CpTI.

3 Claims, No Drawings

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
      (A) ORGANISM: PsMTa Linker (xi) SEQUENCE DESCRIPTION: SEQ ID NO: 1:

Val Ile Leu Gly Val Gly Pro Ala Lys Ile Gln Phe Glu Gly
1              5                    10

(2) INFORMATION FOR SEQ ID NO: 2:

```
      (i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: galactose oxidase linker (xi) SEQUENCE DESCRIPTION: SEQ ID NO: 2:

Gln Ala Ser Ser Tyr Thr Ala Pro Gln Pro Gln
1               5                   10

(2) INFORMATION FOR SEQ ID NO: 3:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: oligo P1

(xi) SEQUENCE DESCRIPTION: SEQ ID NO: 3:

ATGTCGAGCG ACGGACGGCC GGTGCTTGGC                                          30

(2) INFORMATION FOR SEQ ID NO: 4:

(i) SEQUENCE CHARACTERISTICS:
          (A) LENGTH: 48 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: oligo P2

(xi) SEQUENCE DESCRIPTION: SEQ ID NO: 4:

GATCTTCGCC GGACCGACGC CAAGAATCAC GGCATTTGCA CTGGCATC                      48

(2) INFORMATION FOR SEQ ID NO: 5:

(i) SEQUENCE CHARACTERISTICS:
          (A) LENGTH: 48 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO
```

```
        (iv) ANTI-SENSE: NO (vi) ORIGINAL SOURCE:
             (A) ORGANISM: oligo P3

(xi) SEQUENCE DESCRIPTION: SEQ ID NO: 5:

GTCGGTCCGG CGAAGATCCA GTTTGAAGGT AGTAATCATC ATGATGAC                   48

(2) INFORMATION FOR SEQ ID NO: 6:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: oligo P4

(xi) SEQUENCE DESCRIPTION: SEQ ID NO: 6:

TTCTTACTCA TCATCTTCAT CCCTGGACTT GC                                   32

(2) INFORMATION FOR SEQ ID NO: 7:

(i) SEQUENCE CHARACTERISTICS:
             (A) LENGTH: 45 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: oligo P5

(xi) SEQUENCE DESCRIPTION: SEQ ID NO: 7:

CTGGGGGGCT GTGTAAGAAC TAGCTTGGGC ATTTGCACTG GCATC                     45

(2) INFORMATION FOR SEQ ID NO: 8:

(i) SEQUENCE CHARACTERISTICS:
             (A) LENGTH: 45 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: oligo P6

(xi) SEQUENCE DESCRIPTION: SEQ ID NO: 8:

AGTTCTTACA CAGCCCCCCA GCCTGGTAGT AATCATCATG ATGAC                     45

(2) INFORMATION FOR SEQ ID NO: 9:
```

-continued

```
    (i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

ACTATGGATC CAGTAATCAT CATGATGACT C                                             31

(2) INFORMATION FOR SEQ ID NO: 10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 10:

ATATTAAGCT TTTCTTACTC ATCATCTTC                                                29

(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: modified galactose oxidase linker (xi) SEQUENCE DESCRIPTION: SEQ ID NO: 11:

Gln Ala Ser Ile Glu Gly Arg Tyr Thr Ala Pro Gln Pro Gln
1               5                   10

(2) INFORMATION FOR SEQ ID NO: 12:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: natural immunoglobulin linker
```

-continued

```
        (xi) SEQUENCE DESCRIPTION: SEQ ID NO: 12:

Lys Glu Ser Gly Ser Val Ser Ser Glu Gln Leu Ala Gln Phe Arg Ser
1               5                   10                  15

Leu Asp (2) INFORMATION FOR SEQ ID NO: 13:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: linker peptide (xi) SEQUENCE DESCRIPTION: SEQ ID NO: 13:

Glu Gly Lys Ser Ser Gly Ser Gly Ser Glu Ser Lys Pro
1               5                   10

(2) INFORMATION FOR SEQ ID NO: 14:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: linker peptide (xi) SEQUENCE DESCRIPTION: SEQ ID NO: 14:

Gly Gly Gly Gly Ser Gly Gly Gly Ser Gly Gly Gly Gly Ser
1               5                   10                  15

(2) INFORMATION FOR SEQ ID NO: 15:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: oligo P7

(xi) SEQUENCE DESCRIPTION: SEQ ID NO: 15:

ACATGTCGAA TTCTTAGGCA TTTGCACTGG C                                     31
```

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: oligo P8

(xi) SEQUENCE DESCRIPTION: SEQ ID NO: 16:

GAGGAGCCCG GGTCGAGCGA CGGA                                              24

(2) INFORMATION FOR SEQ ID NO: 17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: oligo P9

(xi) SEQUENCE DESCRIPTION: SEQ ID NO: 17:

CTCGAACTCT AGAAGAGAAT TGGCCTTGTT GTG                                  33

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: oligo P10

(xi) SEQUENCE DESCRIPTION: SEQ ID NO: 18:

AATTCTCTTC TAGAGTTC                                                        18

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

-continued

```
    (iv) ANTI-SENSE: NO (vi) ORIGINAL SOURCE:
         (A) ORGANISM: oligo P11

(xi) SEQUENCE DESCRIPTION: SEQ ID NO: 19:

AAACCATGGA TGTTCAAGGA GCTC                                              24

(2) INFORMATION FOR SEQ ID NO: 20:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 20:

TCTATCGAAG GTCGC                                                        15

(2) INFORMATION FOR SEQ ID NO: 21:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 21:

Ser Ile Glu Gly Arg
1               5
```

METHOD OF IMPROVING NEMATODE RESISTANCE IN PLANTS VIA TRANSFORMATION WITH A DNA ENCODING A PROTEINASE INHIBITOR FUSION PROTEIN the present invention discloses a method of improving pathogen resistance or tolerance of a plant in that the plant is transformed with a transgene encoding a fusion protein of two or more proteins or protein domains which are capable of improving pathogen resistance or tolerance when expressed on their own. The invention is exemplified by codelivery of two distinct proteinase inhibitors as a fusion protein in *Arabidopsis thaliana* leading to improved resistance or tolerance of plant parasitic nematodes. For purposes of the present invention, it is recognized that transgenic plants obtained according to the present invention can be tolerant or resistant not only to nematodes but also to viruses, fungi, bacteria, insects, mites, and the like.

Nematodes are the principal animal parasites of plants causing global losses to agriculture estimated at >$100 billion each year. Improved plant resistance to parasitic nematodes is highly desirable to reduce the need for nematicides some of which belong to the most unacceptable pesticides used in agriculture. There are several possible approaches for developing transgenic plants with improved nematode resistance which include anti-invasion and migration strategies, feeding-cell attenuation and anti-nematode feeding strategies (Atkinson et al., Tibtech 13:369–374, 1995). This latter approach can utilize proteinase inhibitors (PIs) which are an important element of natural plant defence strategies (Ryan, Annu Rev Phytopathol 28:425–49, 1990). There are ten PI groups characterised from plants spanning all four classes of proteinases, namely cysteine-, serine-, metallo- and aspartyl-proteinases (Richardson, Methods in Plant Biochemistry 5: 259–305, 1991). EP-A-502 730 discloses that effective, PI-based transgenic defences can be achieved for nematodes. One of the preferred attributes of Pis in nematode control is their small size. The potential of Pis for transgenic crop protection is enhanced by a lack of harmful effects of many PIs when consumed by humans. cDNAs encoding cysteine and serine digestive proteinases of a cyst nematode have been cloned, their major proteolytic activity has been localised to the intestine, and the Pis CpTI and oryzacystatin (Oc-I) have been shown to be effective against these proteinases. Site-directed mutagenesis led to an improved $K_i$ of Oc-I following the deletion of one amino acid. This modified cystatin (Oc-IΔ86) has enhanced efficacy as a transgene against potato cyst-nematode (Urwin et al., Plant J 8:121–131, 1995). When expressed in Arabidopsis it limits growth of both the cyst nematode Heterodera schachtii, and the root-knot nematode Meloidogyne incognita.

Progeny of a cross of transgenic tobacco expressing CpTI and pea lectin, respectively, showed additive efficacy against tobacco budworm (Boulter et al. Crop Protection, 9:351–354, 1990). Tandem promoter/gene constructs might achieve a similar result without the need for crossing plants. Nature suggests at least two further alternative ways of achieving expression of more than one inhibitor, namely bifunctional inhibitors (Wen et al, Plant Mol Biol 18:813–814, 1992) and multi-domain Pis (Waldron et al., Plant Mol Biol 23:801–812, 1993).

It is the object of the present invention to provide methods for the improvement of pathogen resistance or tolerance by delivering more than one resistance or tolerance effector protein. For the purpose of the present invention resistance describes the effect of an introduced transgene to restrict or prevent pathogen multiplication in or on the transgenic plant. Tolerance relates to the ability of the transgenic plant to withstand or recover from damaging effects of pathogen attack and to yield well. Both resistance to and tolerance of a pathogen result in reduction of damage to the crop caused by the pathogen.

The invention thus provides:

A method of improving pathogen resistance or tolerance in a plant and its descendant plants comprising integrating into the genome of said plant a gene encoding a fusion protein comprising (a) a first protein or protein domain with anti-pathogenic activity:

(b) a linker peptide; and (c) a second protein or protein domain with anti-pathogenic activity.

In particular, the invention provides methods, genes and proteins as mentioned before, wherein further proteins or protein domains with anti-pathogenic activity are fused to the fusion protein by linker peptides at least one of the proteins or protein domains with antipathogenic activity has proteinase inhibitor activity at least one of the proteins or protein domains with anti-pathogenic activity is the proteinase inhibitor Oc-IΔD86 at least one of the proteins or protein domains with antipathogenic activity is the proteinase inhibitor CpTI the gene is functionally linked to a promoter sequence driving expression preferentially in plant roots the linker peptide comprises an amino acid sequence which is proteolytically cleaved by the plant the linker peptide comprises an amino acid sequence which is proteolytically stable in the plant the linker peptide is characterized by comprising the amino acid sequence QASSYTAPQPQ (SEQ ID NO:2)

the linker peptide is characterized by comprising the amino acid sequence VILGVGPAKIQFEG (SEQ ID NO:1)

the linker peptide is characterized by comprising the amino acid sequence QASIEGRYTAPQPQ (SEQ 1D NO: 11)

nematode resistance or tolerance is improved

The invention further provides transgenic plants that are obtainable by the method mentioned before. In particular, the invention provides:

a plant expressing a fusion protein encoded by a DNA molecule according to the invention In addition, the invention allows use of the DNA molecules described to improve pathogen resistance or tolerance of a plant and its descendant plants.

To assist in the understanding of the present invention frequently used terms are explained in more detail below:

A plant refers to any plant, particularly to seed plants. The structural and physiological unit of plants are plant cells, comprising a protoplast and a cell wall. The term 'plant cell' refers to any cell which is either part of or derived from a plant. Examples of cells include differentiated cells that are part of a living plant; differentiated cells in culture; undifferentiated cells in culture; the cells of undifferentiated tissue such as callus or tumors; differentiated cells of seeds, embryos, propagules or pollen. In particular, the plant cell may be in form of an isolated single cell or a cultured cell, or as a part of higher organized unit such as, for example, a plant tissue, or a plant organ.

A group of plant cells can be organized into a structural and functional unit called plant tissue. This term includes, but is not limited to, plant organs, plant seeds, tissue culture and any groups of plant cells organized into structural and/or functional units.

Plant material refers to leaves, stems, roots, flowers or flower parts, fruits, pollen, pollen tubes, ovules, embryo sacs, egg cells, zygotes, embryos, seeds, cuttings, cell or tissue cultures, or any other part or product of a plant.

A plant or cell having stably incorporated recombinant DNA in its genome will be referred to as transgenic plant or cell.

Transformation refers to the introduction of a nucleic acid into a cell, particularly to the stable integration of a DNA molecule into the genome of an organism of interest.

Said recombinant DNA refers to one or more DNA molecules formed by joining DNA segments from different sources and obtained using recombinant DNA technology as described, for example, by Sambrook et al., in: "Molecular Cloning-A Laboratory Manual", 2nd edition, Cold Spring Harbor Laboratory Press, NY, USA (1989). Recombinant DNA technology produces recombinant DNA in vitro and transfers it into cells where it can be expressed or propagated (See, Concise Dictionary of Biomedicine and Molecular Biology, Ed. Juo, CRC Press, Boca Raton (1996)), for example, transfer of DNA into a protoplast(s) or cell(s) in various forms, including, for example, (1) naked DNA in circular, linear or supercoiled forms, (2) DNA contained in nucleosomes or chromosomes or nuclei or parts thereof, (3) DNA complexed or associated with other molecules, (4) DNA enclosed in liposomes, spheroplasts, cells or protoplasts or (5) DNA transferred from organisms other than the host organism (ex. *Agrobacterium tumefaciens*). These and other various methods of introducing the recombinant DNA into cells are known in the art and can be used to produce the transgenic cells or transgenic plants of the present invention. The initial insertion of the recombinant DNA into the genome of a $R^0$ plant is not accomplished by traditional plant breeding methods but by technical methods as described herein. Following the initial insertion, transgenic descendants can be propagated using essentially traditional breeding methods.

A gene is considered to describe a discrete chromosomal region comprising a regulatory DNA sequence responsible for the control of expression of a coding sequence which is transcribed and translated to give a distinct polypepfide or protein. In particular, a gene refers to a coding sequence and associated regulatory sequences wherein the coding sequence is transcribed into RNA such as mRNA, rRNA, tRNA, snRNA, sense RNA or antisense RNA. Examples of regulatory sequences are promoter sequences, 5' and 3' untranslated sequences and termination sequences. Further elements that may be present are, for example, introns.

A coding sequence is considered to describe the sequence of a DNA molecule which, when transcribed and translated, results in the formation of a polypeptide or protein.

Expression refers to the transcription and/or translation of an endogenous gene or a transgene in plants. In the case of antisense constructs, for example, expression may refer to the transcription of the antisense DNA only.

A DNA molecule containing at least two heterologous parts, e.g., parts derived from pre-existing DNA sequences which are not associated in their pre-existing states, is sometimes called a chimeric gene. Said molecules are preferably generated using recombinant DNA technology.

In particular, heterologous as used herein means "of different natural or of synthetic origin". For example, if a host cell is transformed with a nucleic acid sequence that does not occur in the untransformed host cell, that nucleic acid sequence is said to be heterologous with respect to the host cell. The transforming nucleic acid may comprise a heterologous promoter, heterologous coding sequence, or heterologous termination sequence. Alternatively, the transforming nucleic acid may be completely heterologous or may comprise any possible combination of heterologous and endogenous nucleic acid sequences.

The method according to the present invention is based on the construction of genes encoding a fusion of effector proteins or protein domains and is exemplified with respect to nematode control by constructs fusing the Pis CpTI and Oc-IΔD86. Said Pis are chosen because they show different inhibitory characteristics resulting in distinguishable effects against cyst nematodes. Thus, CpTI influences sexual fate and Oc-IΔD86 suppresses growth, particularly of developing female nematodes. Transgenic expression of said fusion proteins leads to reduction of the invading pathogen population over a single generation as determined for nematodes by new egg formation by at least 25% and preferably 50%. In the absence of a measurable loss in reproductive success the loss of yield caused by a pathogen can at least be reduced by 25%, preferably 50%.

The principal of the approach centres on the use of peptide linkers that allow both PIs to be translated as a fusion protein. The properties of the linker determine the mode of delivery, that is as a fusion protein or separately due to proteolytic cleavage. Such linker strategies have broad potential that extends beyond nematode control. They offer a novel basis for stacking defence genes to enhance the efficacy and durability of transgenic resistance or tolerance approaches.

To improve pathogen resistance or tolerance the method according to the present invention comprises integrating into the genome of a plant a gene encoding a fusion protein comprising
 (a) a first protein or protein domain with anti-pathogenic activity;
 (b) a linker peptide;
 (c) a second protein or protein domain with anti-pathogenic activity; and
 (d) optionally one or more proteins or protein domains with anti-pathogenic activity fused thereto by one or more peptide linkers.

Preferred proteins or protein domains with anti-pathogenic activity are Pis, *Bacillus thuringiensis* toxins, pathogenesis related proteins, chitinases, glucanases, peptides including lytic peptides, thionins, collagenases, lipases, lectins, ribosomal inactivating proteins, pectinase inhibitors, lipase inhibitors, ot-amylase inhibitors, polygalacturonidase inhibitor protein, patatin, permatin, lysozyme, cholesterol oxidase, viral coat protein, antibodies, single chain antibodies, the products of avirulence genes and resistance genes and other proteins reducing the reproductive success of or damage caused by insects, nematodes, viruses, bacteria, or fungi. The fused proteins or protein domains are not known to occur as fusion proteins in nature. Their corresponding gene sequences are preferably derived from the genome of more than one organism and require recombinant DNA technology to bring them together. Compared to multiples of the same effector domain which achieves an actual increase of effector concentration, distinct domains of two or more effector proteins allow for the possibility of synergistic or additive effects. If one or more of the proteins or protein domains corresponds to a domain encoded by a specific genomic region of the plant to be transformed, integration of the fusion construct according to the present invention will certainly occur within a different genomic region. Particularly preferred are proteins or protein domains with anti-pathogenic activity against more than one pathogen of a crop or anti-pathogenic proteins which counter disease associations such as those between Fusarium and Meloidogyne.

Certain nematodes induce feeding sites involving plant cell modification and feeding at one site for several hours or considerably more. They include species of the genera Meloidogyne Globodera, Heterodera, Rotylenchulus, Tylenchulus, Naccobus, Xiphinama, Longidorus, Paralongidorus, Cryphodera, Trophotylenchulus, Hemicycliophora, Criconemelia, Verutus and Heliocotyjenchus. Genera considered to feed for a more restricted period at one site include Pratylenchus, Radopholus, Hirschmanniella, Trichodorus, Paratdichodorus, Ditylenchus, Aphelenchoides, Scutellonema, and Belonolaimus. With respect to control of species of the above genera and other phytophagous genera of dorylaimid and tylenchid nematodes PIs, collagenases, pectinase inhibitors, lectins, patatin, and cholesterol oxidase are of particular interest. Many PIs are seed storage proteins which accumulate during development of the seed and may occur as one of the most abundant proteins in mature seed. Inhibitors of cysteine or serine digestive proteinases localized in the intestine of nematodes may be preferred for use in the invention. Cysteine proteinases are of particular interest as they are not mammalian digestive enzymes. Particularly effective is oryzacystatin (Oc-I). Site-directed mutagenesis of Oc-I led to an improved $K_i$ following the deletion of one amino acid. This modified cystatin (Oc-IΔD86) has enhanced efficacy as a transgene against potato cyst-nematode (Urwin et al., Plant J 8:121–131, 1995). When expressed in Arabidopsis it limits growth of both *Heterodera schachtii*, a cyst nematode, and *Meloidogyne incognita*, a root-knot nematode. The effect of a single PI on members of the two principal groups of economic nematodes allows for a broad resistance strategy to control very different nematode pests of a target crop. This contrasts the restricted range of target species associated with many natural resistance genes. For instance the HI resistance present in cultivars such as Maris Piper provides qualitative resistance against one potato cyst nematode (Globodera rostochiensis) but no protection against a second closely related species (*G. palida*).

The function of the linker peptide is to join the anti-pathogenic proteins or protein domains without disturbing their function. Natural linkers generally have a length of about 3 to 15 amino acids. Pentapeptides with only Gly, Ser and Thr occur most often in natural linkers and make the best general linkers. Glycine provides flexibility and the other two are polar to interact with solvent or hydrogen bonding to their main chain nitrogen. This achieves some confonmational and energetic stability. They are unlikely to interact with some other part of the joined proteins or protein domains and unlikely to be susceptible to cleavage by host proteases. Also considered favourable are Ala, Pro, Asp, Lys, Gln, and Asn. Hydrophobic residues are avoided such as Arg and Glu, the largest of the basic and acidic residues, respectively. Linkers susceptible to cleavage by widely distributed proteases often have one or more of said unfavourable constituents. For example Gly-Gly-X, wherein X is often an amino acid residue with a hydrophobic side chain, can be a proteolytic processing site. These matters and a list of potentially useful linkers are described in Argos, P, *J. Mol. Biol*. 211, 943–958, 1990. The value of having a cleavable linker is not considered. Linkers have been used in a wide range of fields. The most pertinent for this invention is the use of linkers to express functional antibody molecules such as single chain antibodies in plants. Both complete and engineered antibodies have been expressed in plants. Single chain Fv fragments (ScFv) of antibodies can be engineered by linking the variable heavy chain ($V_H$) and variable light chain domains ($V_L$) of an antibody gene ($V_L$). One approach of achieving this is by using a peptide linker. A number of peptides have been designed using a computer-assisted programme and a search of libraries of three-dimensional peptide sequences. A successful linker is a natural immunoglobulin linker with adjacent residues having the amino acid sequence KESGSVSSEQLAOFRSLD (Bird et al Science 242 423–427, 1988;SEQ ID NO: 12). Another peptide having the amino acid sequence EGKSSGSGSESKP (Bird etalScience 242 423–427, 1988;SEQ ID NO: 13) is dominated by Gly, Ser and Thr. It has been used successfully to express an ScFv in plants (Owen et al Biotechnology 10, 790–794; 1992). A linker with the amino acid sequence GGGGSGGGGSGGGGS (SEQ ID NO: 14) has been recommended for ScFv antibodies based on determining the Euclidean distance between the C-terminus of the VW domain and and the N-terminus of the V, domain (Huston at al *Proc. Natl. Acad Sci* 85, 5879–5883; 1988). This linker has flexibility and yet retains stability and conformation in solution (Argos, P, *J. Mol. Biol*. 211, 943–958, 1990).

In one embodiment of the present invention the coding regions of the Pis Oc-IΔD86 and CpTI are arranged in tandem and joined in-frame by a peptide linker sequence designed to be susceptible to proteolysis. The peptide linker sequence used corresponds to 14 amino acids (VILGVGPAKIQFEG; SEQ ID NO: 1) of the central 'spacer' region of the pea metallothionein-like protein PsMTa (Evans et al., FEBS 262:29–32, 1990). This 'spacer' region is known to be proteinase sensitive (Kille et al., FEBS 295:171–175, 1991 and Tommey et al., FEBS 292:48–52, 1991). Both CpTI and Oc-IΔD86 were present predominantly as separate proteins when expressed in transgenic Arabidopsis. Many other proteins have been reported to be proteolytically sensitive and several recognition sequences have been characterised (Uhlen et al, Meth Enzymol 185:129–143, 1990 and Foresberg et al, J Prot Chem 11:201–211, 1992).

A natural precedent for the use of a proteolytically sensitive linker is the potato multicystatin, PML, which comprises eight tandem cystatin domains linked by sequences susceptible to proteolytic cleavage (Waldron et al, Plant Mol Biol 23:801–812, 1993). However, PML is not known to fragment in planta, but it is stored as inactive crystals in the subphellogen layer of tubers. It is believed to gain activity after being fragmented in the gut of certain insects. It is not suitable for use against nematodes that are unlikely to ingest this protein of 86.8 kDa.

Stigma of the ornamental tobacco *Nicotiana alata* contains an unusual PI (NA-PI-II). It is expressed as a precursor protein of a predicted 41.6 kDa that is cleaved at six sites to produce seven peptides. All but peptide 1 have the same size and share a N-terminal sequence but peptide 7 may not have a functional inhibitory site for either chymotrypsin or trypsin inhibition. The processing sites resulting in release of functional PIs have not been a determined.

Molecules which undergo similar processing exist in animal systems, too, one example being profilaggrin, involved in the terminal differentiation of mammalian epidermis.

In another embodiment of the present invention the coding regions of the Pis Oc-IΔD86 and CpTI are arranged in tandem and joined in-frame by a peptide linker sequence designed to be refractory to proteolysis. The linker peptide used corresponds to an 11 amino acid stretch (QASSYTAPQPQ; SEQ ID NO: 2) of the fungal enzyme galactose oxidase linking the first two domains of the enzyme. This region is known to be structurally rigid (Ito et al, Nature 350:87–91, 1991) and there is no evidence of proteolytic cleavage suggesting that the linker is not susceptible to rapid proteolysis. In Arabidopsis, the construct directs expression of a fusion protein of Oc-IΔD86 and CpTI which remains primarily intact as a 23 kDa protein. Other, semi-rigid linkers have been reported such as that of glucoamylase 1 (Kramer et al, J Chem Soc Farad Trans 89:2595–2602, 1993) which can be used to perform the same function. The sequence of the galactose oxidase linker can be modified to become susceptible to proteolytic cleavage. Thus the modified linker sequence QASIEGRYTAPQPQ (SEQ ID NO: 11) is proteolytically cleaved in a fungal expression system.

The coding sequence of a fusion protein according to the present invention is operably linked to a plant expressible promoter. Preferable promoters include constitutive, inducible, temporally regulated, developmentally regulated, chemically regulated, tissue-preferred and/or tissue-specific promoters.

Preferred constitutive promoters include the CaMV 35S and 19S promoters (Fraley et U.S. Pat. No. 5,352,605). An additionally preferred promoter is derived from any one of several of the actin genes, which are known to be expressed in most cell types. The promoter expression cassettes described by McElroy et al., *Mol. Gen. Genet.* 231:150–160 (1991) can be easily modified for the expression of the coding sequence and are particularly suitable for use in monocotyledonous hosts.

Yet another preferred constitutive promoter is derived from ubiquitin, which is another gene product known to accumulate in many cell types. The ubiquitin promoter has been cloned from several species for use in transgenic plants (e.g. sunflower—Binet et al. Plant Science 79:87–94 (1991), maize—Christensen et a/ Plant Molec. Biol. 12:619–632 (1989)). The maize ubiquitin promoter has systems and its sequence and vectors constructed for monocot transformation are disclosed in Christiansen et aL, EP-A-342 926.

Tissue-specific or tissue-preferential promoters useful for the expression of the coding sequence in plants, particularly maize and sugar beet, are those which direct expression in root, pith, leaf or pollen. Examples are the TUB1 promoter from *Arabidopsis thaliana* b1-tubulin gene (Snustad et al, Plant Cell 4:549, 1992), the PsMT$_A$ promoter region from the metallothionein like gene of *Pisum sativum* (Evans et al, FEBS Letters 262:29, 1990), the RPL16A and ARSK1 promoters from *Arabidopsis thaliana* and further promoters disclosed in WO 97/20057 and WO 93/07278. Another useful promoter is the wun1 promoter fragment of potato (Siebertz et al, Plant Cell 1:961–968, 1989) which is induced in tissues surrounding sites of wounding. Further, chemically inducible promoters are useful for directing the expression and are also preferred (See WO 95/19443).

In addition to promoters, a variety of transcriptional terminators can be used in chimeric genes according to the present invention. Transcriptional terminators are responsible for the termination of transcription beyond the transgene and Its correct polyadenylation. In one preferred embodiment, the coding sequence is operably linked to its naturally occurring polyadenylation signal sequence. Appropriate transcriptional terminators and those which are known to function in plants include the CaMV 35S terminator, the tml terminator, the pea rbcS E9 terminator and others known in the art. Convenient termination regions are also available from the Ti-plasmid of *A. tumefaciens*, such as the octopine synthase and nopaline synthase termination regions. See also, Rosenberg at al., *Gene*, 56:125 (1987); Guerineau etal., *Mol. Gen. Genet.*, 262:141–144 (1991); Proudfoot, *Cell*, 64:671–674 (1991); Sanfacon etal, *Genes Dev.*, 5:141–149; Mogen etal., *Plant Cell*, 2:1261–1272 (1990); Munroe et al, *Gene*, 91:151–158 (1990); Ballas et al., *Nucleic Acids Res.* 17:7891–7903 (1989); Joshi et al., *Nucleic Acid Res.*, 15:9627–9639 (1987)).

Numerous sequences have been found to enhance gene expression from within the transcriptional unit and these sequences can be used in conjunction with a coding sequence to increase expression in transgenic plants. Various intron sequences have been shown to enhance expression, particularly in monocotyledonous cells. For example, the introns of the maize AdhI gene have been found to significantly enhance the expression of the wild-type gene under its cognate promoter when introduced into maize cells (Callis et al, Genes Develop. 1:1183–1200 (1987)). Intron sequences are routinely incorporated into plant transformation vectors, typically within the non-translated leader.

The constructs can also include a regulator such as a nuclear localization signal (Kalderon et al. Cell 39:499–509 (1984); and Lassner et al., *Plant Molecular Biology* 17:229–234 (1991)), plant translational consensus sequence (Joshi, C.P., *Nucleic Acids Research* 15:66436653 (1987)), an intron (Luehrsen and Walbot, *Mol. Gen. Genet.* 225:81–93 (1991)), and the like, operably linked to the appropriate nucleotide sequence.

Preferably, the 5' leader sequence is included in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T.R., and Moss, *Proc. Natl. Acad. Sci. USA* 86:6126–6130 (1989)); potyvirus leaders, for example, TEV leader (Tobacco Etch Virus) (Allison et al., MDMV leader (Maize Dwarf Mosaic Virus); *Virology*, 154:9–20 (1986)), and human immunoglobulin heavy-chain binding protein (BiP), (Macejak, D.G., and Samow, P., *Nature* 353:90–94 (1991); untranslated leader from the coat protein mRNA of alfalfa mosaic virus (AMV RNA 4) (Jobling, S. A., and Gebrke, L., *Nature*, 325:622–625 (1987)); tobacco mosaic virus leader (TMV) (Gallie, D. R. et al., *Molecular-Biology ofRNA*, pages 237–256 (1989)); and maize chlorotic mottle virus leader (MCMV) (Lommel, S. A. et al., *Virology* 91:382–385 (1991)). See also, Della-Cioppa et al., *Plant Physiology* 84:965–968 (1987).

(Ho et al, *Gene* 77:51–59, 1989,and Horton et al, *Gene* 77 61–68, 1989) using primers PI and P4.This results in Oc-IΔD86 and CpTI being separated by the cleavable linker with the amino acid sequence VIL GVGPA KIQ FEG (SEQ ID NO: 1), where the arrows indicate putative cleavage sites (Oc-IΔD86\PsMTa\CPTI fusion protein). Genes encoding fusion proteins as described above can be introduced into plant cells in a number of art-recognized ways. Those skilled in the art will appreciate that the choice of method might depend on the type of plant targeted for transformation. Suitable methods of transforming plant cells include microinjection (Crossway et al., *BioTechniques* 4:320–334 (1986)), electroporation (Riggs et al., *Proc. Natl. Acad. Sci. USA* 83:5602–5606 (1986), Agrobactedurrumediated transformation (Hinchee et al., Biotechnology 6:915–921 (1988);

See also, Ishida et al, *Nature Biotechnology* 14:745–750 (June 1996) for maize transformation), direct gene transfer (Paszkowski et al., *EMBO J.* 3:2717–2722 (1984); Hayashimoto et al., *Plant Physio.* 93:857–863 (1990)(rice)), and ballistic particle acceleration using devices available from Agracetus, Inc., Madison, Wis. and Dupont, Inc., Wilmington, Del. (see, for example, Sanford et al., U.S. Pat. No. 4,945,050;and McCabe et al., *Biotechnology* 6:923–926 (1988)). See also, Weissinger et al., *Annual Rev. Genet.* 22:421–477 (1988); Sanford et al, Particulate Science and Technology 5:27–37 91987)(onion); Svab et al, *Proc. Natl. Aced. Sci. USA* 87:8526–8530 (1990) (tobacco chloroplast); Christou et al., *Plant Physiol.* 87:671–674 (1988)(soybean); McCabe et al, *Bio/Technology* 6:923–926 (1988)(soybean); Klein et al, *Proc. Natl. Aced. Sci. USA*, 85:4305–4309 (1988)(maize); Klein et al., Bio/Technology 6:559–563 (1988) (maize); Klein et al, *Plant Physiol.* 91:440–444 (1988) (maize); Fromm et al, *Bio/Technology* 8:833–839 (1990); and Gordon-Kamm et al., *Plant Cell* 2:603–618 (1990) (maize); Koziel et al., *Biotechnology* 11:194–200 (1993)(maize); Shimamoto et al., *Nature* 338:274–277 (1989) (rice); Christou at al., *Biotechnology* 9:957–962 (1991) (rice); Datta et al., *Bio/Technology* 8:736–740 (1990) (rice); European Patent Application EP-A-332 581 (orchardgrass and other Pooideae); Vasil et al., *Biotechnology* 11:1553–1558 (1993) (wheat); Weeks et al., *Plant Physiol.* 102:1077–1084 (1993) (wheat); Wan et al., Plant Physiol. 104:37–48 (1994)(barley); Jahne t al., *Theor. AppL Genet.* 89:525–533 (1994)(barley); Umbeck et al., Bio/Technology 5:263–266 (1987)(cotton); Casas et al., *Proc. Natl. Acad. Sci. USA* 90:11212–11216 (Dec. 1993) (sorghum); Somers et al., *Bio/Technology* 10:1589–1594 (December 1992)(oat); Torbert at al., *Plant Cell Reports* 14:635–640 (1995)(oat); Weeks et al., *Plant Physiol.* 102:1077–1084 (1993)(wheat); Chang et al., WO 94/13822 (wheat) and Nehra et al., *The Plant Journal* 5:285–297 (1994)(wheat).

One particularly preferred embodiment for the introduction of recombinant DNA molecules into sugar beet by Agrobactenurnmediated transformation can be found in Konwar, J. Plant Biochem & Biotech 3:37–41,1994.

Methods using either a form of direct gene transfer, particle gun technology or Agrobacteriuomediated transfer usually, but not necessarily, take advantage of a selectable or screenable marker which provides resistance to an antibiotic (e.g., kanamycin, hygromycin or methotrexate) or a herbicide (e.g., phosphinothricin). The choice of selectable or screenable marker for plant transformation is, however, not critical to the invention. Examples are the nptII gene which confers resistance to kanamycin and related antibiotics (Vieira & Messing, *Gene* 19:259–268 (1982); Bevan et al., *Nature* 304:184–187 (1983)), the bargene which confers resistance to t phosphinothricin (White et al., *Nucl. Acids Res.* 18:1062 (1990), Spencer et al., *Theor. Appl. Genet.* 79:625631 (1990)), the hph gene which confers resistance to the antibiotic hygromycin (Blochlinger & Diggelmann, *Mol. Cell. Bio.* 4:2929–2931), and the dhfr gene, which confers resistance to methotrexate (Bourouis and Jarry, *EMBO J.* 2:1099–1104 (1983)). Transformation can be undertaken with DNA species (i.e. co-transformation) and both these techniques are suitable for use with for example PI coding sequences.

Further embodiments of the present invention are the fusion protein described above comprising (a) a first protein or protein domain with anti-pathogenic activity;

(b) a linker peptide;

(c) a second protein or protein domain with anti-pathogenic activity; and (d) optionally one or more further proteins or protein domains with anti-pathogenic activity fused thereto by one or more peptide linkers, and DNA constructs encoding said proteins which can be used to improve pathogen resistance or tolerance of a plant and its descendant plants defined as sexually or asexually derived future generation plants including, but not limited to, progeny plants.

Pathogens such as nematodes cause economic loss to most of the world's crops. These include for temperate agriculture; potatoes, sugarbeet, vegetable crops (including tomato, cucumber, cabbage, cauliflower, celery, lettuce, carrot, beets, parsnip radish, chickpea and lentil) oiseed crops, grain legumes, maize, wheat, barley, oat, rye and other cereals, grassland and forage crops (including a range of grasses red and white clover and luceme), forest trees, deciduous and nut trees, soft fruit and vines including grapevines, ornamental and bulb crops, garlic, onions and glasshouse crops.

These also include subtropical and tropical crops such as rice, other cereals (including wheat, barley, maize, oats, sorghum and millet), root and tuber crops (including potato, sweet potato, cassava, yams, taro), food legumes, vegetables (including tomato, cucumber, gherkin, cantaloupes and other melons, watermelon, cabbage, cauliflower, chillies, eggplant, garlic, onions celery, pumpkins, sashes and gourds, lettuce, chickpea and lentil) peanut, citrus, subtropical and tropical fruit trees, coconut and other palms, coffee, cocoa, tea, bananas, plantains and abaca, sugarcane, tobacco, pineapple, cotton and other tropical fibre crops and also a range of spices.

Said dicotyledonous or monocotyledonous plants transgenically expressing the fusion proteins according to the present invention constitute a further preferred embodiment of the present invention as well as the descendants of said plants and their seed. Further comprised is a commercial bag comprising seed of said plants. Preferred is a commercial bag together with lable instructions for the use of the seed contained therein. The genetic properties engineered into the plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic equipment, yield harvested product of better quality than products which were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD), methalaxyl (Apron), and pirimiphos—methyl (Actellic). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation.

Other methods of application are also possible such as treatment directed at the buds or the fruit.

It is a further aspect of the present invention to provide new agricultural methods such as the methods exemplified above which are characterized by the use of transgenic plants, transgenic plant material, or transgenic seed according to the present invention which is described in further detail in the following non-limiting examples. In these examples, procedures for making, manipulating and analyzing nucleic acids are carried out by standard procedures as described by Sambrook et al., in: "Molecular Cloning-A Laboratory Manual", 2nd edition, Cold Spring Harbor Laboratory Press, NY, USA (1989).

EXAMPLES

Example 1
Generadon of Dual Inhibitor Expression Cassettes

Fusion proteins containing both the Oc-IΔD86 and CpTI coding regions separated by a linker sequence is generated by a two-step PCR procedure. The Oc-IΔD86 coding region is PCR amplified from a pre-existing construct (Urwin et al, *Plant J* 8:121–131, 1995) using oligonucleotide primer PI(5'-ATGTCGAGCGACGGACGGCCGGTGCTTGGC-3'; SEQ ID NO: 3), corresponding to the 5' end of the coding region, and a second primer P2 (5'-GATCTTCGCCGGACCGACGCCAAGAATCACGGCAT-TTGCACTGGCATC-3'; SEQ ID NO: 4), complementary to the 3' end of the Oc-IΔD86 coding region and to the 5' portion of the underlined protease cleavable linker sequence obtainable from the plant metallothionein-like PsMTa gene sequence (Evans et al, *FEBS* 262:29–32, 1990). Similarly the CpTI gene of the binary vector pROK/CpU+5 containing the CpTI cDNA under the control of the CaMV 35S promoter (Hilder et al, *Nature* 330:160–163, 1987) is amplified with primer P3 (5'-GTCGGTCCGGCGAAGATCCAGTTTGAAGGTA-GTAATCATCATGATGAC-3'; SEQ ID NO: 5) designed to encode the 3' portion of the underlined protease cleavable PsMTa linker sequence and the 5' end of the CpTI coding region together with P4 (5'-TTCTTACTCATCATCTTCATCCCTGGACTTGC-3'; SEQ ID NO: 6), complementary to the 3'-end of the CpTI coding region. The amplified Oc-IΔD86 and CpTI sequences contain an 18 bp complementary region at their 3' and 5' ends respectively and are joined together by the PCR technique of SOEing (Ho et al, *Gene* 77:51–59, 1989,and Horton et al, Gene 77 6168, 1989) using primers P1and P4. This results in Oc-IΔD86 and CpTI being separated by the cleavable linker with the amino acid sequence VIL GVGPA KIQ FEG (SEQ ID NO: 1), where the arrows indicate putative cleavage sites (Oc-IΔD86 PsMTa CPTI fusion protein A similar procedure is used to generate a DNA fragment encoding Oc-1AD86 and CpTI with an intervening non-cleavable linker (Oc-IΔD86/go/CpTI fusion protein) obtained from the galactose oxidase gene sequence (McPherson et al. 1992) on the one hand using a primer pair consisting of PI above and P5 (5'-CTGGGGGGCrGTGTAAGAACTAGCTTGGGCAMGC-ACTGGCATC-3'; SEQ ID NO:7) and on the other hand a primer pair consisting of P6 (5'-AGTFCT TACACAGCCCCCCAGCCTGGTAGTAATCATCATGAT-GAC- 3'; SEQ ID NO:8) and P4 above (sequence encoding the linker is underlined). This non-cleavable linker sequence encodes a peptide with the sequence QASSYTAPQPQ (SEQ ID NO:2).

Example 2
Generation of Single Inhibitor Expression Cassettes The sequence encoding the mature cowpea trypsin inhibitor (CPTI) is amplified from plasmid pUSSR (Hilder et al, Nature 220:160–163, 1987) by the polymerase chain reaction using oligonucleotide primers designed from the published sequence but with restriction enzyme sites (underlined) added to assist cloning into the expression vector. The two primers are 51-ACTATGGATCCAGTAATCATCATGATGACTC-3, (SEQ ID NO: 9) and 5'-ATATTAAGCTTTTCTTACTCATCATCTTC-3' (SEQ ID NO: 10). The 246 bp product is cloned directly into the expression vector pQ3O ("CQlAexpression" system, Qiagen) utilizing the BamHI and Hindlll sites incorporated into the primers. The sequence encoding Oc-I is amplified from genomic DNA of Oryza sativa L. japonica by the polymerase chain reaction using primers P7 (5'-ACATGTCGAATTCTTAGGCATTTGC ACTGGC-3'; SEQ ID NO: 15) and P8 (5'-GAGGAGCCCGGGTCGAGCGACGGA-3'; SEQ ID NO: 16). The intron is removed by the PCR technique of gene SOEing (Ho et al supra), wherein the primer pairs P7/P9 (5'-CTCGAACTCTAGAAGAGAATTGGCCTTGTTGTG-3'; SEQ ID NO: 17) and P8/P10 (5'-AATTCTCTTCTAGAGTTC-3'; SEQ ID NO: 18) are used to amplify the two exons. These products are then SOEn together by amplifying with primers P7 and P8 and the product cloned into SmaVEcoRi digested Bluescript. Subsequently the engineered Oc-I gene is cloned into the type IV pQE expression vector (Qiagen) using the BamHI/Hindil sites.

The 'Unique Site Elimination' strategy (Pharmacia) is used to generate a single codon change within the Oc-I gene using primer P11 (5'-AAACCATGGATGTTCAAGGA-GCTC-3'; SEQ ID NO: 19).

Example 3

Plant Transformation

The pBI-derived plasmids are introduced into competent *Agrobacterum tumefaciens* LBA4404 by electroporation as described by Shen and Forde, Nucleic Acids Res 17:83–85, 1989. Subsequently they are introduced into *Arabidopsis thaliana* ecotype C24 by A. tumefaciens-mediated transformation of roots as described by Clarke et al, Plant Mol Biol Rep 10:178–189, 1992. T1 seed is collected from individual plants using Aracons of Beta-Tech, Gent, Belgium, to ensure self-fertilisation. Arabidopsis harbouring 35S/Oc-IΔD86 (Urwin et al, *The Plant Journal* 12, 455–461, 1997) was also used in this study.

Example 4

E. coli Expression

Expression from both the single and dual effector constructs is carried out as described by Urwin et al, *Plant J* 8:121–131, 1995. The proteins are expressed as fusion proteins containing a 6xHis N-terminus as encoded by the pQ30 and pQE32 vector, respectively, and purified using nickel resin, with the exception of CpTI released from the Oc-IΔD86/PsMTa/CpTI fusion protein. In the latter case a crude homogenate is assayed after the removal of Oc-IΔD86 using the 6-His-tag. Inhibition levels of crude homogenate from untransformed *E. coli* is subtracted from these CpTI samples. Oc-IΔD86 is detected with the polyclonal antibody described by Urwin et al. (Urwin et al, 1995,supra) and CpTI with a monoclonal antibody generated according to Liddell and Cryer, "A practical guide to monoclonal antibodies", John Wiley and Sons, New York, USA, page 188,1991.

Papain and trypsin are used in the cysteine and serine proteinase inhibition assays respectively, essentially as described by Abrahamson et al, J Biol Chem 262:9688–9694, 1987 using the substrate N-Cbz-Phe-Arg-7-amido-4-methylcoumarin. Fluorescence is measured with a Perkin Elmer SL50B spectrofluorimeter having a plate reader attachment.

Example 5

Detection of Expression and Uptake by Nematodes

Proteins expressed in *E. coli* are purified using the QIAexpress system (Qiagen, Hilden, Germany) as described by Urwin et al, 1995,Urwin et al., Plant J 8:121–131, 1995.

Arabidopsis total protein fractions suitable for SDS PAGE analysis are obtained by homogenising root material with a mortar and pestle prior to being taken up in 0.15 M NaCl, 10 mM HEPES, and 10 mM EDTA pH 7.4.Protein samples are solubilised by boiling in SDS PAGE loading buffer (15% βmercaptoethanol, 15% SDS, 1.5% bromophenol blue, 50% glycerol) prior to electrophoresis. PI expression is analysed by western blot analysis as described by Urwin et al. (*The Plant Journal* 12, 455461, 1997) utilising a horse-radish-peroxidase conjugated antibody to facilitate use of the horseradish peroxidase chemiluminescent (HRPL) system which is used according to the manufacturer's instructions (National Diagnostics, Atlanta, Ga. The soluble protein fraction is collected by extracting ground plant material in buffer (0.15 M NaCl, 10 mM Hepes, 10 mM EDTA pH 7.4). Insoluble material is pelleted at 75,000 rpm for 15 mins (Beckman Optima centrifuge, using a TLA100.2 rotor) to separate soluble (cytosol) and insoluble material. The pellet is vigorously resuspended in 100 mM sodium carbonate pH 11,centrifuged as above and the supernatant containing the membrane associated proteins collected. The pellet is washed in said carbonate buffer and resuspended in SDS-PAGE loading buffer. All samples were boiled in SDS-PAGE loading buffer prior to electrophoresis.

Western blot analysis is also used to demonstrate the uptake of inhibitors by nematodes from transgenic plants. Feeding females are collected by manually picking them off Arabidopsis roots, thereby ensuring the absence of contaminating plant material. About 70 nematodes are collected from plants expressing a single or dual Pis. Nematodes are ground in an microfuge tube and resuspended in 0.15 M NaCl, 10 mM Hepes, 10 mM EDTA pH 7.4,containing a mix of commercially available protease inhibitors (Boehringer Mannheim, Lewes, UK). Samples are boiled with SDS PAGE loading buffer and western blot analysis carried out as described above.

Antibodies raised against CpTI and OcIΔD86 react with protein bands of the correct $M_r$ in homogenates of Arabidopsis expressing single PI constructs. Neither antibody cross-reacts to a detectable extent with either the non-cognate PI in plant homogenates or with other proteins present in the sample. In both *E. coli* and Arabidopsis root homogenates the Oc-IΔD86/go/CpTI construct yields one major product of c23 kDa which is recognised by both antibodies and thus contains both PIs. A weaker signal corresponding to the lower molecular weight individual PI was detected with each antibody, indicating a low level of dissociation of the fusion protein. The Oc-IΔD86/ PsMTa/ CpTI construct yields a reversed western blot pattern showing a higher reactivity with the lower M, than the higher M, products. This suggests that cleaved Pis predominate in this case. Relative inhibition assays are carried out on the products of Oc-IΔD86PsMTacpti and Oc-IΔD86/go/CpTI produced in *E. coli*. Both provide 95% inhibition of papain and trypsin activity suggesting that the tandem PI molecule inhibits both proteinases and that the two Pis are still effective after cleavage of the PsMTa-derived linker.

Western blot analysis is performed on root homogenates of a range of transformed lines. For each of the four constructs, one line is selected for further study. Each line selected expresses the target PI(s) at 0.4% total protein. Analysis of inhibitor uptake by nematodes with both antibodies reveals that females of *M. incognita* ingest Oc-IΔD86 or CpTI when parasitising plants expressing single PI constructs. Also the intact fusion protein Oc-IΔD86/go/CpTI is detected by both antibodies. Simultaneously each antibody detects a smaller product corresponding to single PIs. Surprisingly no products of the expected size are detected in nematodes isolated from plants expressing the Oc-IΔD86/ PsMTa/CpTI construct. The results for *H. schachtii* are similar to those for *M. incognita* with the exception that the uncleaved product of Oc-IΔD86/go/CpTI cannot be detected within the nematodes. The failure to detect products from Oc-IΔD86/PsMTa/CpTI in nematodes is unexpected given that both inhibitors are present in the host plant. Western blot analysis of differentially fractionated plant material demonstrates that both products of Oc-IΔD86/PsMTa/CpTI are membrane associated but are not integral membrane proteins.

Example 6
Nematode Infection, Recovery, and Measurement

Populations of *H. schachtii* are maintained on cabbage plants. Four week old cabbage plants are infected by repotting the plants into a sand/loam mix harbouring *H. schachtii* eggs at a density of 30 eggs $g^{-1}$. Cabbage plants are grown at 22° C. under normal day length. The infected soil used to grow these plants is recovered and the number of eggs $g^{-1}$ counted. A 3-fold serial dilution with 50% loam/sand mixture is made using a soil divider and this is then used to grow wild type C24 Arabidopsis. In preliminary experiments an egg count of 9 eggs $g9^{-1}$ was found to give the highest, 5-fold increase. However, in subsequent infections only 5 eggs $g^{-1}$ was used to ensure good infection without overstressing the plants.

Populations of *M. incognita* are maintained on tomato plants, grown on a 16 h day at 24° C. Whole root balls of infected plants are chopped into small pieces and used to prepare a serial dilution in 50% loam/sand mixture. Aliquots of the serial dilutions are used to establish optimal infection rate, with the bulk of the "soil" being held at 10° C.

Clean infected root material and cysts are collected by growing the plants in a 50% sandI loam mixture. Manual collection of nematodes at early time points is facilitated by staining the roots with acid tuchsin as described by Urwin et al. (Urwin et al, *The Plant Journal* 12, 455–461, 1997), with the exception that the thin Arabidopsis roots do not require a clearing step. Collection of cysts is carried out using a Seinhorst elutriator (Seinhorst 1964). Female fecundity is determined by manually counting the number of eggs from all the individuals collected from a group of plants.

Infected Arabidopsis plants are grown with 16 h day length, at an irradiance of 6 mmol photons $m^{-2} s^{-1}$ at 22° C. in Sanyo MLR3500 growth cabinets. Plant pots containing wild-type C24 Arabidopsis and those containing plants expressing inhibitors are placed in random grids.

Example 7
Modification of the Galactose Oxidase Linker

The amino acid sequence of the linker region between domain 1 and domain 2 of galactose oxidase is modified by replacing the three amino acid codons AGT TCT TAC encoding the amino acid sequence SSY with the sequence TCT ATC GAA GGT CGC (SEQ ID NO: 20) encoding the amino acid sequence SIEGR (SEQ ID NO: 21). The first codon simply replaces the existing Ser codon while the remaining four codons encode a Factor Xa proteolytic cleavage site. The PCR-based mutagenesis procedure used is described in Baron et al, *J Biol Chem* 269, 25095–25105, 1994.The modified galactose oxidase gene is expressed in *Aspergillus nidulans*. Surprisingly two protein bands are found on an SDS-PAGE gel, corresponding to sizes of domain 1 (about 16 kDa) and domains 2+3 (about 52 kDa). No protein is dectected at a position corresponding to full-length galactose oxidase. The results demontrastes that the modified galactose oxidase linker is susceptible to cleavege plant proteinases. The use of this linker or further modifications of it should allow plant proteinases to process multimeric molecules in planta.

While the forgoing invention has has been described in some detail for purposes of clarity and understanding, it will be appreciated by one skilled in the art from reading of this disclosure that various changes in form and detail can be made without departing from the true scope of the invention and the following claims.

What is claimed is:

1. A method of improving resistance or tolerance in a plant and its descendant plants to a nematode, comprising:
   (i) integrating into a genome of a plant a DNA molecule encoding a fusion protein, wherein said fusion protein comprises
      (a) a first protein, or protein domain, with anti-pathogenic activity, wherein said first protein or protein domain comprises Oc-IΔD86 or Oc-I;
      (b) a linker peptide comprising an amino acid sequence characterized by at least one of SEQ ID NO: 1, SEQ ID NO: 2 or SEQ ID NO: 11; and
      (c) a second protein, or protein domain, with anti-pathogenic activity, wherein said second protein or protein domain comprises CpTI;

thus producing a plant with improved nematode resistance or tolerance; and optionally (ii) generating a descendant plant.

2. The method according to claim 1, wherein said fusion protein further comprises at least one additional protein or protein domain fused by at least one additional linker peptide to at least one of said first protein or protein domain, said linker peptide, and said second protein or protein domain.

3. The method according to claim 1, wherein said DNA molecule comprises a promoter sequence capable of driving expression preferentially in roots.

* * * * *